United States Patent [19]

Colombo

[11] Patent Number: 4,965,426
[45] Date of Patent: Oct. 23, 1990

[54] APPARATUS FOR INSTANTANEOUSLY DESTROYING USED INJECTION SYRINGE NEEDLES

[76] Inventor: Giovanni Colombo, Via Trevano, 49, CH-6900 Lugano, Switzerland

[21] Appl. No.: 318,625

[22] Filed: Mar. 3, 1989

[30] Foreign Application Priority Data

Mar. 8, 1988 [IT] Italy ............................... 19693 A/88

[51] Int. Cl.⁵ .......................... B23H 9/00; H05B 3/00
[52] U.S. Cl. .......................................... 219/68; 83/16; 128/919
[58] Field of Search .................. 219/68, 69.12; 83/15, 83/580, 16; 128/919; 303.1, 303.13, 303.14, 303.18, 303.19; 606/26, 35, 38, 44

[56] References Cited

U.S. PATENT DOCUMENTS 4,628,169 12/1986 Ch'ing-Lung ........................... 83/15

FOREIGN PATENT DOCUMENTS 8704379 7/1987 PCT Int'l Appl. .............. 219/69.12
233810 10/1977 U.S.S.R. ........................... 219/69.12

Primary Examiner—A. D. Pellinen
Assistant Examiner—Geoffrey S. Evans
Attorney, Agent, or Firm—Bucknam and Archer

[57] ABSTRACT

The apparatus comprises at least a pair of electrodes supplied by an AC power supply, in contact therewith there are arranged, through suitable guide members, the tip and a middle portion of the syringe needle, the power supply to the electrodes being controlled by a switch which, as it is closed, provides an electric current effective to blunt and melt the needle which can not be reused.

3 Claims, 2 Drawing Sheets

APPARATUS FOR INSTANTANEOUSLY DESTROYING USED INJECTION SYRINGE NEEDLES

BACKGROUND OF THE INVENTION

The present invention relates to an apparatus for completely destroying injectin syringe needles immediately upon use.

As is known a used syringe needle may represent a great danger for a person handling the syringe, mainly if the patient is affected by infective deseases.

There are known protective devices, adapted to provide a certain protection against undesired punctures which devices, however have been found affected by drawbacks, the main of which is that they are not able of instantaneously blunt the needle tip in a safe and reliable manner.

SUMMARY OF THE INVENTION

Accordingly, the main object of the present invention is to overcome the above mentioned drawback, by providing an electrical type of apparatus which is able of instantaneously melting, blunting and destroying the needles of used syringes.

Another object of the present invention is to provide such an apparatus which can be easily held in a hand and safely operated.

Another object of the invention is to provide such an apparatus which is effective to surely sterilize used syringe needles.

Yet another object of the present invention is to provide such an apparatus which can be made by using easily available components and materials and which, moreover, is competitive from a mere economic standpoint.

According to one aspect of the present invention, the above mentioned objects, as well as yet other objects, which will become more apparent hereinafter, are achieved by an apparatus for destroying syringe needles immediately after the use, characterized in that said apparatus comprises at least a pair of electrodes supplied by an AC power supply, in contact therewith there are arranged, through guide means, the tip portion and a middle portion of the syringe needle, the power supply to said electrodes being controlled by a switch which, as it is closed, provides an electric current which blunts and melts said needle.

BRIEF DESCRIPTION OF THE DRAWINGS

Further characteristics and advantages of the used syringe needle destroying apparatus according to the present invention will become more apparent hereinafter from the following detailed description of a preferred embodiment of this apparatus, which is illustrated, by way of an indicative but not limitative example, in the figures of the accompanying drawings, where.

DESCRIPTION OF THE PREFERRED EMBODIMENT

Figure 1:
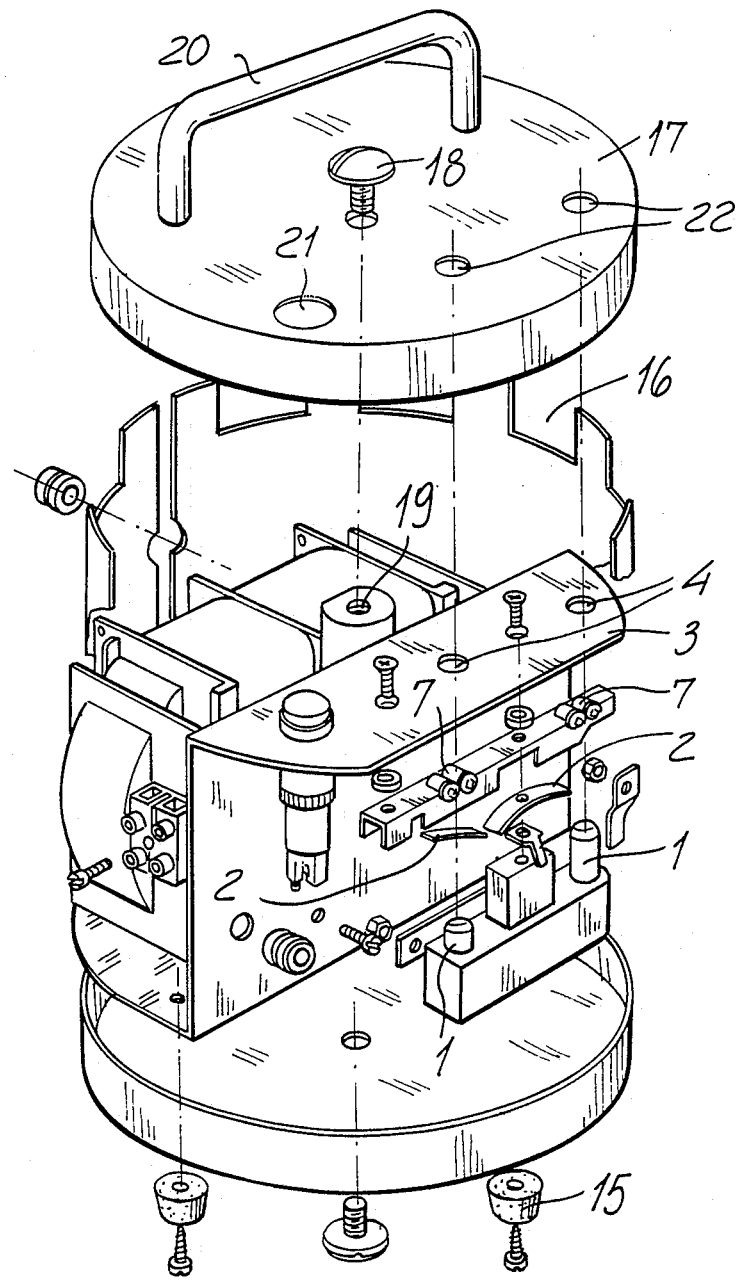
FIG. 1 is a schematic perspective view illustrating the needle destroying apparatus according to the present invention, devoid of a portion of its side casing and with its cover and bottom in a disassembled condition.
Figure 2:
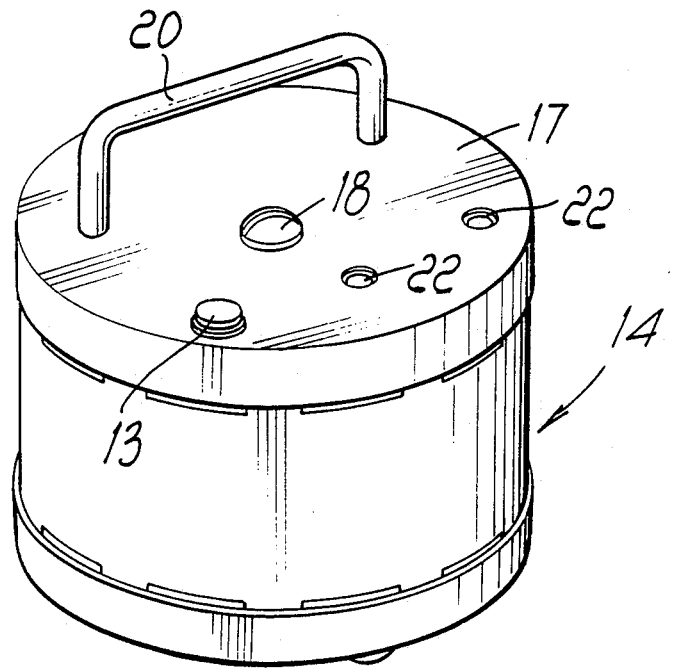
FIG. 2 is an outline view of the casing housing the subject apparatus.
Figure 4:
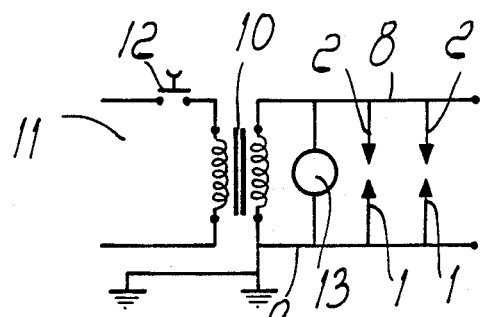
FIG. 4 shows a possible electric diagram of this same apparatus.

With reference to the figures of the accompanying drawings, the apparatus for destroying used syringe needles according to the present invention essentially preferably comprises two pairs of electrodes each consisting of a small carbon block 1 and a flexible reed member 2 which is restrained at one end thereof and has its other end arranged on the perpendicular line to said small carbon block.

More specifically, the two small carbon blocks 1 have a suitably different height, so that there tip portions are arranged at a given distance from a top shelf member 3 which is provided with corresponding holes 4 for receiving the needles 5 of a corresponding number of syringes.

Figure 3:
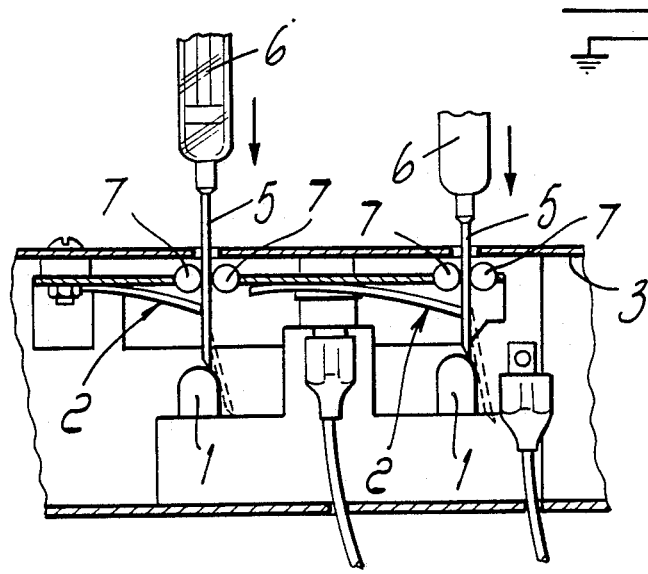
FIG. 3 is a detailed view illustrating the operating portion of the apparatus according to the present invention.

Thus, as is shown in FIG. 3, the subject apparatus will be able of processing needles of different diameters and lengths.

In this connection it should be apparent that the downward stroke of the needles is guided by carbon opposite roller pairs 7.

The electrodes 1 and 2 are respectively power supplied through power supply cables 8 and 9, through a suitable electrical transformer 10 which is coupled to the mains 11 through a switch 12.

Through the power supply circuit, moreover, thre is provided a signalling lamp 13 for indicating the proper operation of the apparatus.

In operation, by arranging a syringe needle in contact with the electrodes and closing the electrical circuit through the mentioned switch, the needle will be subjected to an electrical very great current flow which will bring said needle to a temperature of 2500° C., thereby partially melting said needle, at least at the tip thereof.

Thus, the tip portion will assume a substantially spherical configuration, not dangerous for the skin.

As is shown the apparatus operating components are enclosed in a box-like body, of preferably round cross-section, mounted on foot members 15.

The box-like body is provided with side ventilation slots 16 and is closed by a cover 17 affixed to the inner structure by means of a screw 18, engaging with a corresponding threaded hole 19.

The cover, in turn, is provided with a gripping handle 20 and is provided with a hole 21 for perimetrically restraining the mentioned signalling lamp and holes 22, overlaying the roller pairs 7 for receiving the syringe needles.

From the above disclosure it should be apparent that the invention fully achieves the intended objects.

While the invention has been disclosed and illustrated with reference to a preferred embodiment thereof, it should be apparent that the disclosed embodiment is susceptible to several modifications and variations, all of which will come within the scope and spirit of the appended claims.

I claim:

1. An apparatus for destroying injection syringe needles immediately after use, comprising two pairs of electrodes, supplied with an AC current, in contact therewith there are arranged, through guide means, a tip portion and a middle portion of a syringe needle, a switch for controlling electric power supplied to said two pairs of electrodes, said switch, as closed, providing an electrical current flow adapted to melt and blunt at least said tip portion of said syringe needle, each electrode of said two pairs of electrodes consisting of a small carbon block, a flexible reed member and two carbon rollers, said reed member being pivoted at one end thereof and having its other end arranged on a perpendicular line to said small carbon block, said carbon blocks having different heights so that top portions thereof are arranged at a given distance from a top shelf member provided with a plurality of holes for receiving syringe needles.

2. An apparatus according to claim 1, wherein said carbon rollers are opposite horizontal-axis carbon roller pairs adapted to guide a downward stroke of said needles.

3. An apparatus according to claim 1, wherein said electrodes are supplied by electrical cables through a transformer coupled to an AC source by said switch, said apparatus further comprising a box-like round cross-section casing provided with supporting foot members and ventilation side slots and a closure cover affixed by a screw engaging in a threaded hole, said cover including a gripping handle and a first hole for perimetrically restraining an operation signalling lamp and second holes overlaying said roller pairs for receiving said syringe needles.

* * * * *